United States Patent
Auclair, Jr. et al.

(10) Patent No.: US 9,301,771 B2
(45) Date of Patent: Apr. 5, 2016

(54) SURGICAL HANDPIECE FOR ENDOSCOPIC RESECTION

(75) Inventors: Merle I. Auclair, Jr., Hudson, NH (US); Paul Robert Duhamel, Groton, MA (US); Gheorghe Mihalca, North Chelmsford, MA (US); Yuri E. Kazakevich, Newton, MA (US); Paul C. Young, North Andover, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 12/894,828

(22) Filed: Sep. 30, 2010

(65) Prior Publication Data

US 2011/0245599 A1  Oct. 6, 2011

Related U.S. Application Data

(60) Provisional application No. 61/247,722, filed on Oct. 1, 2009, provisional application No. 61/251,381, filed on Oct. 14, 2009.

(51) Int. Cl.
| | |
|---|---|
| *A61B 17/32* | (2006.01) |
| *A61B 17/16* | (2006.01) |
| *A61B 17/00* | (2006.01) |
| *A61B 17/22* | (2006.01) |
| *A61B 19/00* | (2006.01) |

(52) U.S. Cl.
CPC ........ *A61B 17/32002* (2013.01); *A61B 17/1622* (2013.01); *A61B 2017/0046* (2013.01); *A61B 2017/00464* (2013.01); *A61B 2017/22079* (2013.01); *A61B 2019/4868* (2013.01); *A61B 2217/005* (2013.01)

(58) Field of Classification Search
CPC ............... A61B 17/1622; A61B 17/32002; A61B 2017/00464; A61B 2017/0046; A61B 2017/22079; A61B 2019/4868; A61B 2217/005
USPC ............ 606/106, 107, 159, 167–170; 604/22, 604/44; 600/562, 565
See application file for complete search history.

(56) References Cited

U.S. PATENT DOCUMENTS

| | | | | |
|---|---|---|---|---|
| 4,852,551 | A | * | 8/1989 | Opie et al. ..................... 600/121 |
| 5,413,556 | A | * | 5/1995 | Whittingham ................. 604/22 |

(Continued)

FOREIGN PATENT DOCUMENTS

| | | |
|---|---|---|
| DE | 196 22 486 C1 | 10/1997 |
| DE | 19622486 C1 | 10/1997 |

(Continued)

OTHER PUBLICATIONS

International Preliminary report and written opinion regarding International patent application PCT/US2010/050875 mailed on Apr. 12, 2012.

(Continued)

*Primary Examiner* — Ryan J Severson
*Assistant Examiner* — Rachel S Papeika
(74) *Attorney, Agent, or Firm* — Chapin IP Law, LLC

(57) ABSTRACT

The present disclosure relates to a surgical handpiece including an insert removably coupled to the handpiece, wherein the insert is configured to allow aspiration of fluid and tissue through the insert during a surgical procedure. Other surgical handpieces and a method for the removal of tissue during an endoscopic procedure are also disclosed.

18 Claims, 5 Drawing Sheets

(56) References Cited

U.S. PATENT DOCUMENTS

| | | | |
|---|---|---|---|
| 5,549,565 A * | 8/1996 | Ryan et al. | 604/167.03 |
| 5,624,393 A * | 4/1997 | Diamond | 604/48 |
| 5,692,518 A * | 12/1997 | Baker et al. | 600/556 |
| 5,810,809 A | 9/1998 | Rydell | |
| 5,827,323 A | 10/1998 | Klieman et al. | |
| 5,871,493 A | 2/1999 | Sjostrom et al. | |
| 6,007,497 A * | 12/1999 | Huitema | 600/567 |
| 6,068,603 A * | 5/2000 | Suzuki | 600/565 |
| 6,120,462 A * | 9/2000 | Hibner et al. | 600/566 |
| 6,436,067 B1 | 8/2002 | Deng et al. | |
| 6,585,664 B2 * | 7/2003 | Burdorff et al. | 600/564 |
| 6,620,111 B2 * | 9/2003 | Stephens et al. | 600/567 |
| 2001/0047183 A1 | 11/2001 | Privitera et al. | |
| 2003/0216686 A1 * | 11/2003 | Lynch et al. | 604/93.01 |
| 2004/0034281 A1 * | 2/2004 | Cartledge et al. | 600/190 |
| 2004/0204679 A1 * | 10/2004 | Visconti et al. | 604/131 |
| 2005/0065453 A1 * | 3/2005 | Shabaz et al. | 600/564 |
| 2006/0052774 A1 | 3/2006 | Garrison et al. | |
| 2007/0149893 A1 * | 6/2007 | Heske et al. | 600/566 |
| 2008/0269687 A1 * | 10/2008 | Chong et al. | 604/180 |
| 2008/0287925 A1 | 11/2008 | Le et al. | |

FOREIGN PATENT DOCUMENTS

| | | |
|---|---|---|
| DE | 198 59 217 A1 | 12/1998 |
| DE | 18 69 217 A1 | 7/2000 |
| DE | 19859217 A1 | 7/2000 |
| RU | 2528925 C1 | 10/2013 |
| SU | 862234 | 7/1981 |
| WO | WO 97/16124 A1 | 5/1997 |
| WO | WO2008/144552 A1 | 11/2008 |

OTHER PUBLICATIONS

International Search Report and Written Opinion for PCT/US2010/050875 Dated Jan. 31, 2011.
Patent Examination Report No. 1 for Australian Appln. No. 2010300561, dated Jan. 19, 2015.
Decision of Rejection for Japanese Patent Appln. No. 2012-532309, dated Dec. 8, 2014.
Decision of Rejection for Japanese Patent Appln. No. 2012-532309, dated May 7, 2014.
State Intellectual Property Office, P.R. China; First Office Action for Chinese Patent Appln. No. 201080044170, dated Apr. 1, 2014.
Federal Institute for Industrial Property for Russia Patent Application No. 2012116224/14, Sep. 30, 2010.
State Intellectual Property Office, Peoples Republic of China; Second Office Action for Chinese Patent Appln. No. 201080044170.X, dated Dec. 15, 2014.
Federal Service for Intellectual Property, Notification on results of patentability examnination, dated Aug. 4, 2015, 5 pages. (DE 19859217, previously cited).

* cited by examiner

SURGICAL HANDPIECE FOR ENDOSCOPIC RESECTION

CROSS-REFERENCE TO RELATED APPLICATIONS

This application claims priority to U.S. Patent Application Ser. No. 61/247,722 and U.S. Patent Application No. 61/251,381, the disclosures of which are incorporated herein by reference in their entireties.

BACKGROUND

1. Field of Technology

The present disclosure relates to surgical handpieces, and specifically surgical handpieces that provide user friendly cleaning and sterilization.

2. Related Art

Surgical handpieces used to drive cutting tools during a surgical procedure, such as the handpiece and cutting tools shown in U.S. Pat. No. 5,871,493 ('493 patent), which is incorporated herein by reference in its entirety, are currently available. These handpieces have design features that make cleaning and sterilizing of the handpiece a challenge. Specifically, the areas around the cutting tool connection and the entry to the aspiration channel are hard to access and have a potential for not being properly cleaned prior to sterilization. Therefore, handpieces that lend themselves to user-friendly cleaning and sterilization are needed.

SUMMARY

In an aspect, the present disclosure relates to a surgical handpiece including an insert removably coupled to the handpiece, wherein the insert is configured to allow aspiration of fluid and tissue through the insert during a surgical procedure. In an embodiment, the handpiece includes a groove configured for housing of the insert. In another embodiment, the insert includes a distal portion and a proximal portion, wherein the proximal portion is configured for engagement with a suction device. In yet another embodiment, the insert includes at least one tab, wherein the tab is configured for disposal within an opening of the handpiece. In a further embodiment, the insert includes at least two tabs, wherein the tabs are configured for disposal within openings of the handpiece. In yet a further embodiment, the handpiece includes an aspiration channel, wherein the channel is located in-line with the groove so as to allow aspiration of the fluid and tissue through the channel and into the insert.

In an embodiment, the handpiece includes a valve removably coupled to the handpiece, wherein the valve is configured to be located in a first position or a second position. In another embodiment, locating the valve in the first position allows for aspiration of the fluid and tissue through the channel and the insert and locating the valve in the second position does not allow for aspiration of the fluid and tissue through the channel and the insert. In another embodiment, the handpiece includes an access port. In yet another embodiment, the handpiece includes a cover disposed within the access port.

In another aspect, the present disclosure relates to a surgical handpiece including an insert removably coupled to the handpiece, wherein removal of the insert allows for access to an inner area of the handpiece. In an embodiment, the inner area includes a drive shaft and entry to an aspiration channel. In another embodiment, the insert is coupled to the handpiece via a snap-lock assembly.

In yet another aspect, the present disclosure relates to a method for the removal of tissue during an endoscopic procedure. The method includes providing an assembly including a surgical handpiece including an insert removably coupled to the handpiece; and a cutting tool coupled to the handpiece; and inserting the cutting tool into an area of the body to cut the tissue and remove the tissue via the assembly.

In an embodiment, the tissue is removed via the insert. In another embodiment, the method further includes removing the insert from the handpiece and replacing the insert with another insert. In yet another embodiment, a suction device is coupled to the insert for removal of the tissue. In a further embodiment, the method further includes removing the insert from the handpiece to allow for access to an inner area of the handpiece, the inner area including a drive shaft and an aspiration channel. In yet a further embodiment, the method further includes cleaning the inner area of the handpiece. In an embodiment, the surgical handpiece includes an access port and a cover disposed within the access port, wherein the method further includes removing the cover and cleaning an inner area of the handpiece.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings.

DETAILED DESCRIPTION OF THE EMBODIMENTS

The following description of the preferred embodiment(s) is merely exemplary in nature and is in no way intended to limit the disclosure, its application, or uses.

Figure 5:
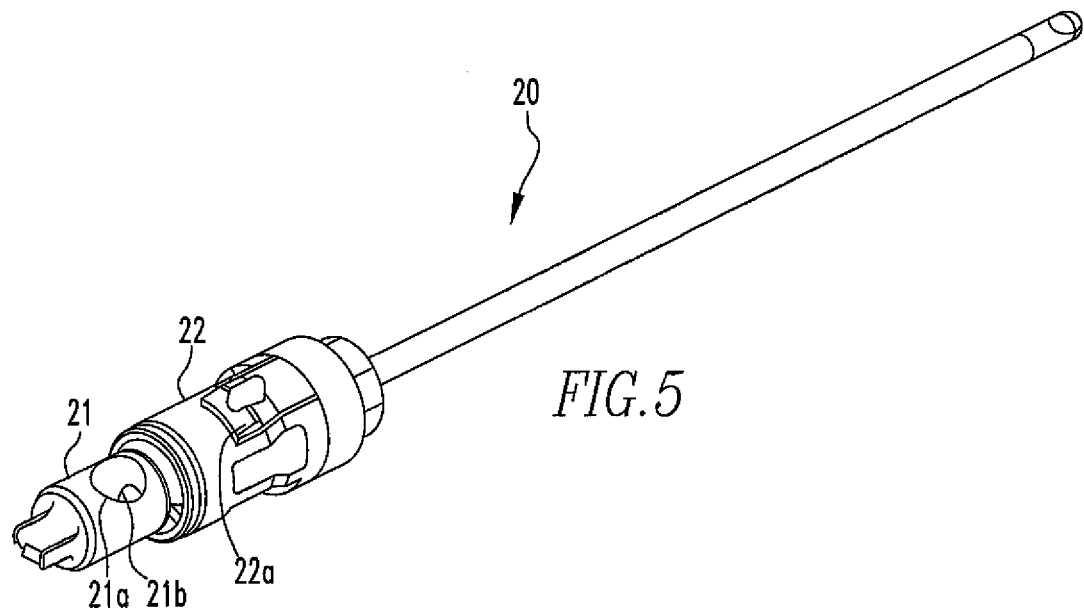
FIG. 5 shows a perspective view of a cutting tool for use with the surgical handpiece of FIG. 1.

FIGS. 1-4 show a first embodiment of the surgical handpiece 10 of the present disclosure. The handpiece 10 includes a body 11 having a distal end 11a and a proximal end 11b. At its distal end 11a, the handpiece 10 includes a cylindrical bore 12 for coupling of a surgical cutting tool 20 (FIG. 5). Within the bore 12 is a drive shaft 13 that is coupled to a motor 14 positioned within the handpiece 10. The handpiece 10 includes pushbutton switches 15 that produce signals for use in controlling the motor 14. The handpiece 10 is employed within a surgical system and method, the components and steps of which are shown and described in the '493 patent. The handpiece 10 is coupled to the rest of the system by a cable 16 that is coupled to the proximal end 11b of the handpiece 10. The cable 16 may be coupled via a connector, such as a threaded connector, as shown and described in the '493 patent.

Figure 1:
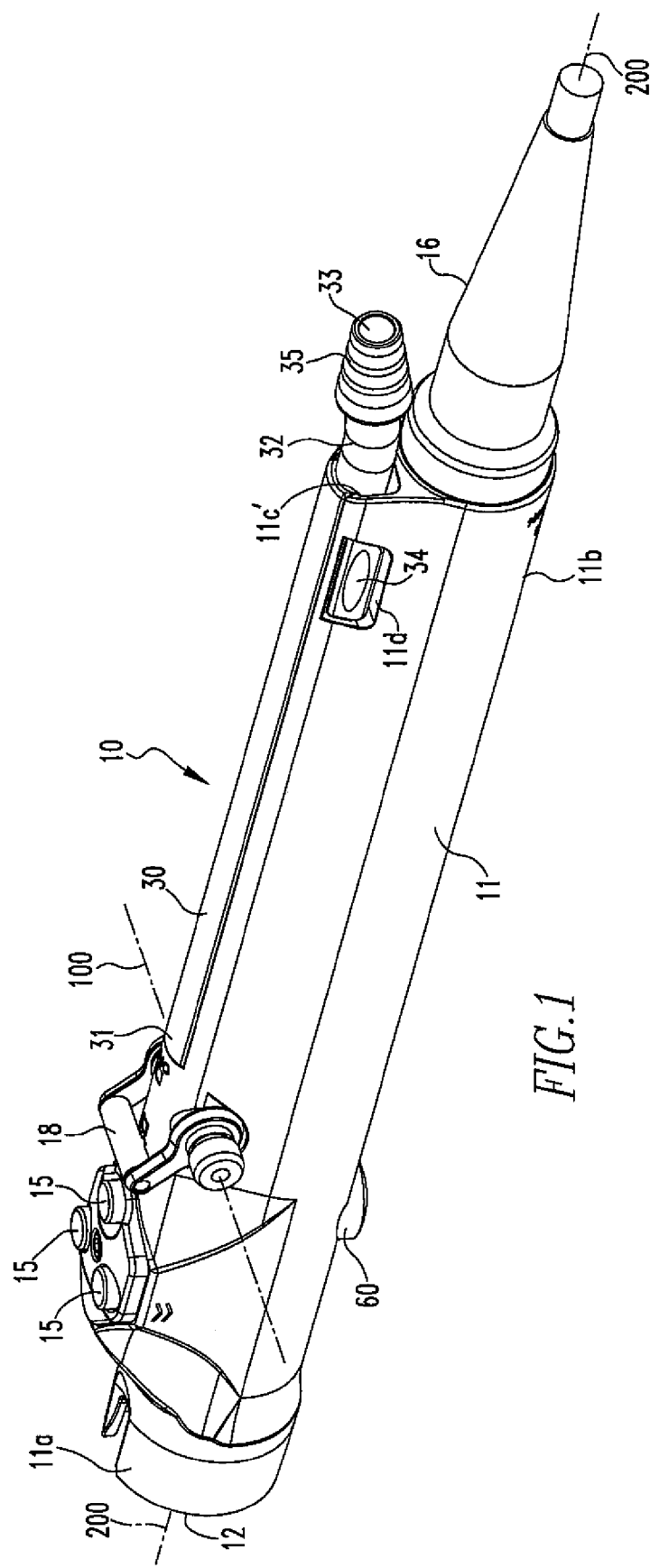
FIG. 1 shows a perspective view of a first embodiment of the surgical handpiece of the present disclosure.
Figure 2:
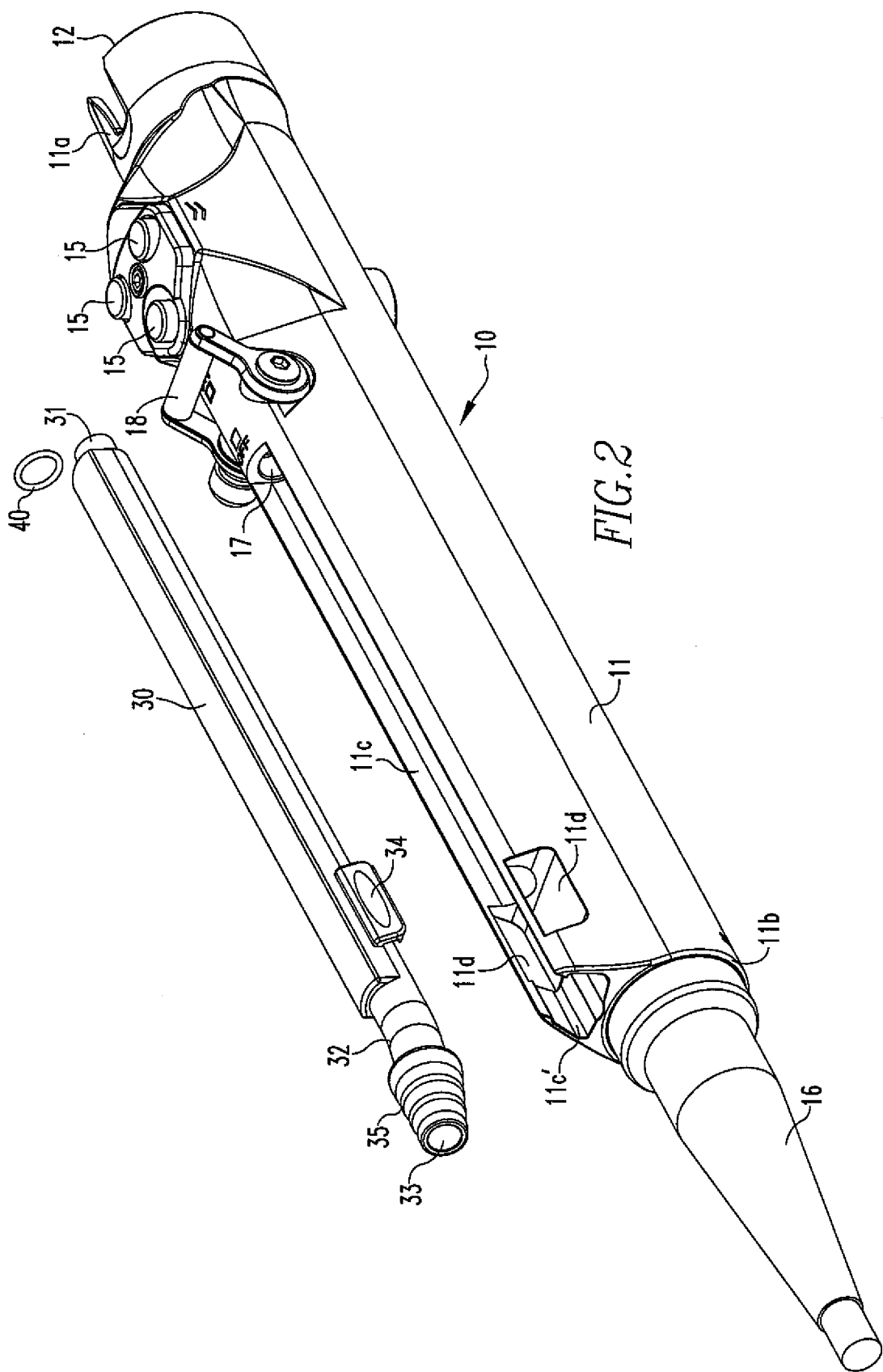
FIG. 2 shows an exploded view of the surgical handpiece of FIG. 1.
Figure 3:
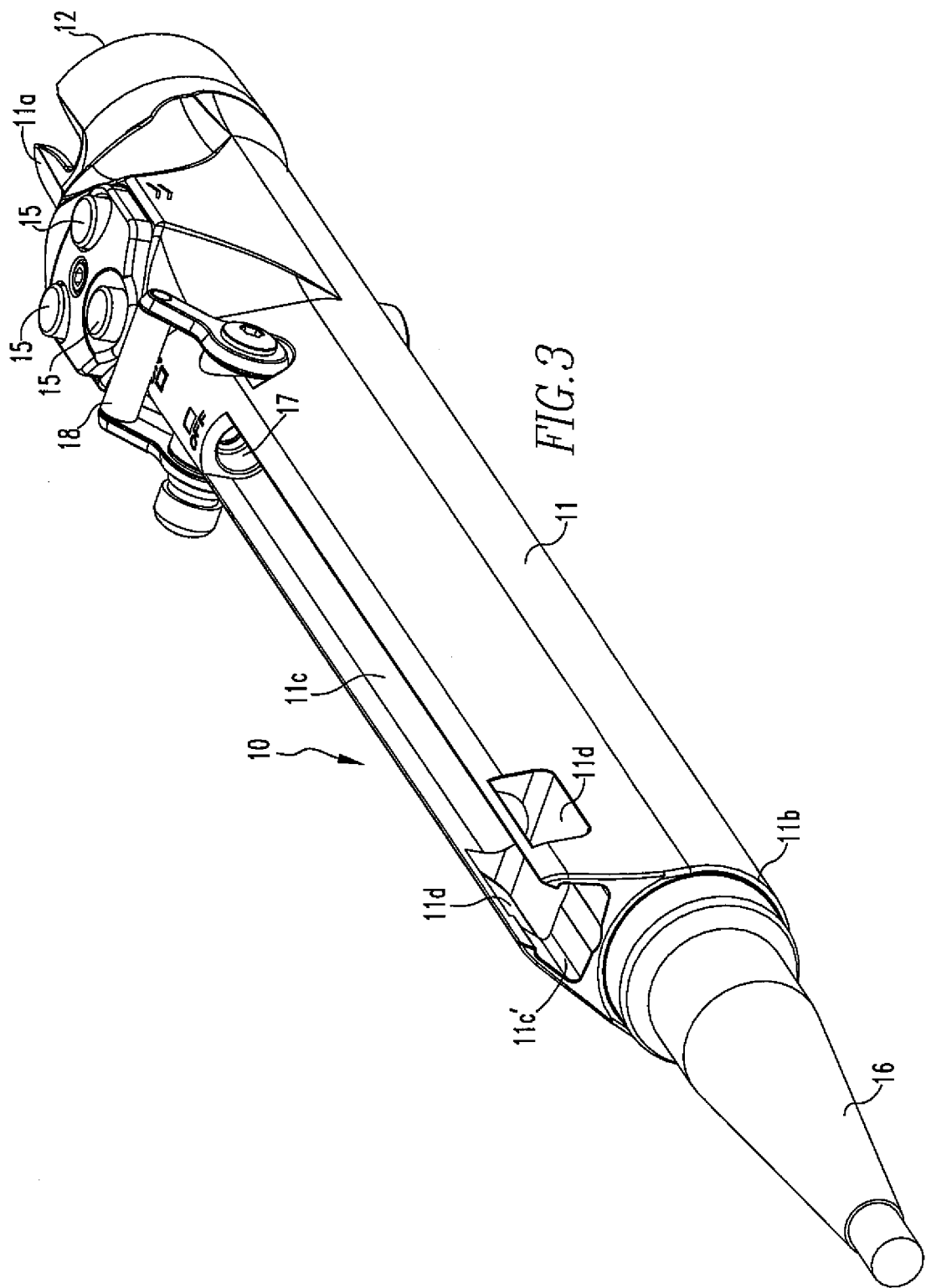
FIG. 3 shows a perspective view of the surgical handpiece of FIG. 1 without the insert.
Figure 4:
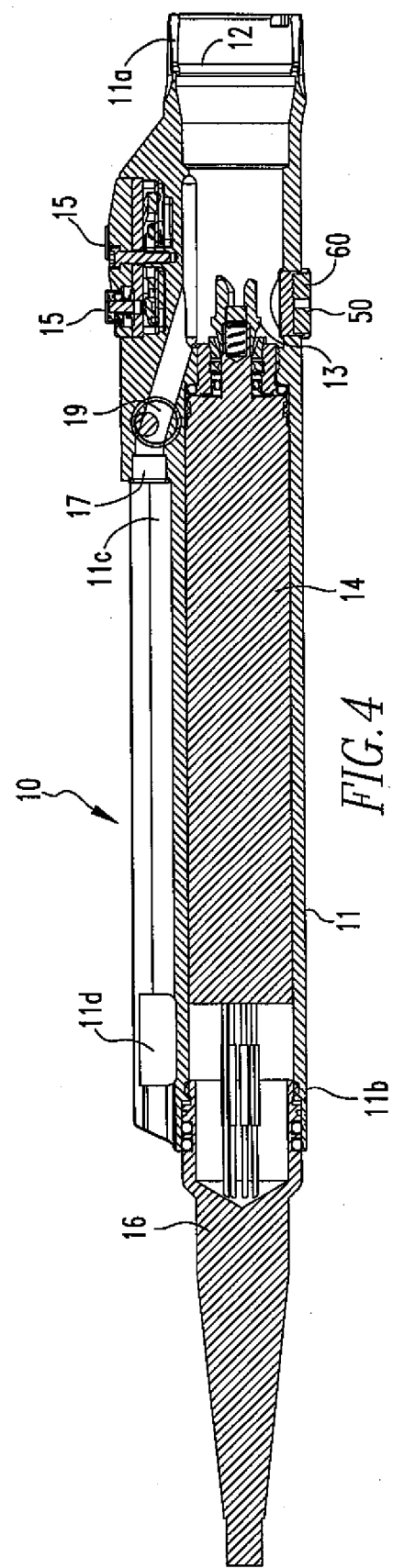
FIG. 4 shows a cross-sectional view of the surgical handpiece of FIG. 1 without the insert.

The surgical cutting tool 20, which is further described in the '493 patent, includes an inner cutting member 21 disposed within an outer cutting member 22. The instrument 20 is coupled to the handpiece 10 to create an assembly such that the hubs 21a,22a of the members 21,22 are disposed within the bore 12. The assembly is used to cut and remove tissue from an area of the body during a surgical procedure. The hub 21a of the inner cutting member 21 includes an opening 21b that permits material, such as fluid and tissue, drawn through member 21 to pass into an aspiration channel 17 of the handpiece 10. The handpiece 10 also includes a handle 18 that controls a valve 19 and thereby controls flow through the aspiration channel 17. The handle 18 rotates about an axis 100 that is perpendicular to a longitudinal axis 200 of the handpiece 10 between a first position, wherein the handle 18 is pushed forward toward the distal end 11a, as shown in FIG. 1, and a second position, wherein the handle 18 is pushed backward toward the proximal end 11b. Having the handle 18 in the first position allows for opening of the valve 19 and having the handle 18 in the second position allows for closing of the valve 19 or vice versa. The handle 18 and valve 19 are both removably coupled to the handpiece 10 via a coupling method described in the '493 patent or other method known to one of skill in the art.

An insert 30 is located within a groove 11c of the body 11 such that the insert 30 is located in-line with the aspiration channel 17. The insert 30 includes a distal end 31, a proximal end 32, a cannulation 33 that extends the entire length of the insert 30, and tabs 34 coupled to the insert 30. The insert 30 is located within the groove 11c such that the tabs 34 are disposed within openings 11d in the body 11. The insert 30 may be placed within the groove 11c by placing the distal end 31 into the groove 11c via the opening 11c' and pushing the insert 30 longitudinally towards the distal end 11a of the handpiece 10 until the tabs 34 are located within the openings 11d. During placement of the insert 30 into the groove 11c, the tabs 34 may be reduced radially, by squeezing the tabs 34 inwardly toward the insert 30 to fit within the opening 11c'. For the purposes of this disclosure, there are two tabs 34 and two corresponding openings 11d. However, there may be only one tab and one corresponding opening or more than two tabs and corresponding openings. It is also within the scope of this disclosure to not have any tabs 34 or openings 11d. An o-ring 40 may be located on the distal end 31 of the insert 30 in order to provide a seal and substantially reduce leakage of fluid and tissue from the aspiration channel 17, as will be further described below.

The proximal end 32 of the insert 30 includes a spigot 35. During use, the spigot 35 is coupled to a source of suction (not shown), such that when the valve 19 is located in an open position, fluid and tissue are aspirated through the insert 30. After use, the insert 30 may be removed from the groove 11c in order to allow access to the aspiration channel 17, especially the portion of the aspiration channel 17 in which the valve 19 is located, thereby allowing the user to clean and sterilize these areas. Once these areas have been cleaned and sterilized, a new insert may be placed within the groove 11c and the old insert may be discarded.

Additionally, the body 11 includes an access port 50 located towards the distal end 11a of the body 11. A cover 60 is located within the access port 50 to close the port 50 during use. After use, the cover 60 is removed in order to allow access to the inner area of the handpiece 10, such as the bore 12 and the components within the bore 12, such as the drive shaft 13, thereby allowing the user to clean and sterilize these areas and components. After these areas are cleaned and sterilized, the cover 60 may also be cleaned and then re-inserted in the port 50.

Figure 6:
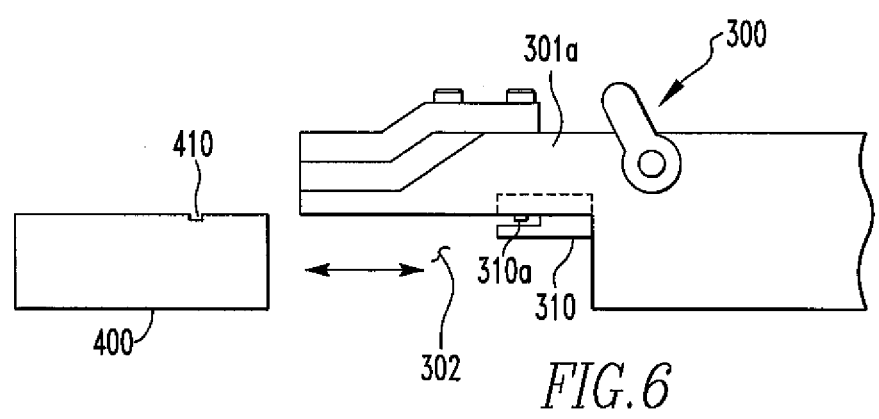
FIG. 6 shows a side view of a second embodiment of the surgical handpiece of the present disclosure.

FIG. 6 shows a cross-sectional view of a second surgical handpiece 300 of the present disclosure. The handpiece 300 is similar to handpiece 10, except for having an insert 400 removably coupled to the distal end 301a of the handpiece 300. The handpiece 300 may or may not additionally have the groove 11c and insert 30 combination of handpiece 10. The handpiece 300 may include a latch 310 having a tab 310a that engages an opening 410 of the insert 400 and acts as a snap-lock assembly to couple the insert 400 to the handpiece 300. Similar to the cover 60 of the handpiece 10, the insert 400 covers the inner area of the handpiece 300, such as the bore 302 and the components within the bore 302, such as the drive shaft and the aspiration channel (not shown). During use, the insert 400 is attached to the handpiece 300. However, after use, the insert 400 is removed to allow the user to clean and sterilize the inner area and its components. After cleaning and sterilization, the insert 400 may also be cleaned and then re-attached to the handpiece 300. However, the insert 400 may be disposed of and another insert may coupled to the handpiece 300.

For the purposes of this disclosure, the inserts 30, 400 of the handpieces 10,300 are plastic. However, other materials could also be used. Also, the inserts 30, 400 may be made via a process, such as injection molding, die drawing, or any other process known to one of skill in the art. The cover 60 is made using similar materials and via similar processes. The groove 11c, openings 11d, and access port 50 may be made via a machining process or another process known to one of skill in the art.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. A surgical handpiece comprising:
   a removable insert coupled to the handpiece, the insert configured to allow aspiration of fluid and tissue through the insert during a surgical procedure and operable for removable decoupling from the handpiece for replacement of the removable insert and open access to the removable insert for sterilization, the removable insert including a distal portion, a proximal portion, a cannulation extending the entire length of the removable insert, and resiliently deformable tabs coupled to the removable insert, the resiliently deformable tabs configured for disposal within openings of the handpiece, the proximal portion including a spigot coupled to a source of suction, the handpiece including:
   a groove in a body of the handpiece, the groove in the body of the handpiece configured for housing of the removable insert;
   an aspiration channel, the aspiration channel in-line with the groove in the body of the handpiece to enable aspiration of the fluid and tissue through the aspiration channel and into the removable insert;
   a removable valve; and the cannulation fludically coupled to the aspiration channel for suctional extraction therethrough, the removable insert forming a sealed and enclosed coupling between the aspiration channel and the suction source.

2. The surgical handpiece of claim 1 wherein the removable valve is configured to be located in a first position or a second position.

3. The surgical handpiece of claim 2 wherein locating the removable valve in the first position allows for aspiration of the fluid and tissue through the channel and the insert and locating the removable valve in the second position does not allow for aspiration of the fluid and tissue through the channel and the removable insert.

4. The surgical handpiece of claim 1 wherein the handpiece includes an access port.

5. The surgical handpiece of claim 4 wherein the handpiece includes a cover disposed within the access port.

6. The surgical handpiece of claim 1 wherein the proximate portion is designed for fluidic coupling with the suction source and the distal portion is designed for fluidic evacuation from a surgical site, the proximate and distal portions defining an enclosure adapted for sealing between the suction source and the aspiration channel.

7. The surgical handpiece of claim 1 wherein the aspiration channel is fluidically coupled to at least one cutting member for directing the suction to the cutting member for extracting material cut by the cutting member.

8. The surgical handpiece of claim 7 wherein the insert is removably coupled by the tabs biased toward engagement of slots for securing the insert.

9. A surgical handpiece comprising:
an insert removably coupled to a body of the handpiece, wherein removal of the insert allows for access to an inner area of the handpiece, the insert including a distal portion, a proximal portion, a cannulation extending the entire length of the insert, and resiliently deformable tabs coupled to the insert, the resiliently deformable tabs configured for disposal within openings of the handpiece, the proximal portion including a spigot coupled to a source of suction;
a removable valve; and
the cannulation fluidically coupled to an aspiration channel for suctional extraction therethrough,
the insert forming a sealed and enclosed coupling between the aspiration channel and the suction source.

10. The surgical handpiece of claim 9 wherein the inner area includes a drive shaft and an aspiration channel.

11. The surgical handpiece of claim 10 wherein the cannulation of the insert is fluidically coupled to the aspiration channel and fluidically separate from the drive shaft.

12. The surgical handpiece of claim 9 wherein the insert is coupled to the handpiece via a snap-lock assembly.

13. A method for the removal of tissue during an endoscopic procedure comprising:
providing an assembly comprising:
a surgical handpiece including an insert removably coupled to the handpiece, the insert operable for removable decoupling from the handpiece for replacement of the insert and open access to the insert for sterilization, the insert including a distal portion, a proximal portion, a cannulation extending the entire length of the insert, and resiliently deformable tabs coupled to the insert, the resiliently deformable tabs configured for disposal within openings of the handpiece, the proximal portion including a spigot coupled to a source of suction; and
a cutting tool coupled to the handpiece; and
inserting the cutting tool into an area of the body to cut the tissue and remove the tissue via the assembly, the handpiece including:
a groove in a body of the handpiece, the groove configured for housing of the insert;
a removable valve;
an aspiration channel, the aspiration channel in-line with the groove in the body of the handpiece so as to allow aspiration of the fluid and tissue through the aspiration channel and into the insert; and
the cannulation fluidically coupled to the aspiration channel for suctional extraction therethrough,
the insert forming a sealed and enclosed coupling between the aspiration channel and the suction source.

14. The method of claim 13 wherein the tissue is removed via the insert.

15. The method of claim 14 wherein a suction device is coupled to the insert for removal of the tissue.

16. The method of claim 13 further comprising removing the insert from the handpiece to allow for access to an inner area of the handpiece, the inner area including a drive shaft and an aspiration channel.

17. The method of claim 16 further comprising cleaning the inner area of the handpiece.

18. The method of claim 13 wherein the surgical handpiece includes an access port and a cover disposed within the access port, wherein the method further comprises removing the cover and cleaning an inner area of the handpiece.

* * * * *